United States Patent [19]

Gower

[11] 4,387,253

[45] Jun. 7, 1983

[54] PREPARATION OF DICHLOROBENZYL ALCOHOL

[75] Inventor: Christopher J. Gower, West Bridgford, England

[73] Assignee: The Boots Company Limited, Nottingham, England

[21] Appl. No.: 292,110

[22] Filed: Aug. 12, 1981

[30] Foreign Application Priority Data

Sep. 3, 1981 [GB] United Kingdom ................ 8028664

[51] Int. Cl.$^3$ ............................................. C07C 33/46
[52] U.S. Cl. ..................................... 568/812; 568/715
[58] Field of Search ................................ 568/715, 812

[56] References Cited

U.S. PATENT DOCUMENTS

| 248,512 | 10/1949 | Wilkinson, Jr. ..................... 568/715 |
| 3,993,699 | 11/1976 | Maeda ................................. 568/812 |
| 4,283,565 | 8/1981 | Bernhardt et al. .................. 568/812 |
| 4,301,088 | 11/1981 | Bernhardt et al. .................. 568/715 |

FOREIGN PATENT DOCUMENTS

| 690105 | 7/1964 | Canada ................................ 568/812 |
| 42-21495 | 1/1967 | Japan .................................. 568/812 |
| 42-25064 | 11/1967 | Japan .................................. 568/715 |
| 812526 | 4/1959 | United Kingdom ............... 568/812 |
| 865672 | 7/1970 | United Kingdom ............... 568/812 |
| 1227144 | 4/1971 | United Kingdom ............... 568/715 |
| 2008098 | 5/1979 | United Kingdom ............... 568/812 |
| 166666 | 2/1964 | U.S.S.R. ............................. 568/715 |

OTHER PUBLICATIONS

Rhoad et al., J.A.C.S., vol. 72, p. 2216 (1950).

*Primary Examiner*—Werren B. Lone
*Attorney, Agent, or Firm*—Lawrence Rosen

[57] ABSTRACT

2,4-Dichlorobenzyl alcohol is obtained in high purity and in high yield by reacting 2,4-dichlorobenzyl chloride in a two stage reaction with a water soluble salt of an organic acid in the presence of a phase transfer catalyst to give the 2,4-dichlorobenzyl ester of the organic acid which is subsequently hydrolysed with a strong base.

4 Claims, No Drawings

PREPARATION OF DICHLOROBENZYL ALCOHOL

This invention relates to the preparation of 2,4-dichlorobenzyl alcohol which is anti-bacterial substance having use inter alia as an industrial biocide and in various medicinal preparations (see, for example, British Patent Specification No. 865672 published in the name of the Boots Pure Drug Company Limited in 1961 and a paper by Carter et al entitled "The Preparation and the Antibacterial and Antifungal Properties of some Substituted Benzyl Alcohols" in The Journal of Pharmacy and Pharmacology 1958 10 (supplement) pp149T to 157T.

According to the present invention there is provided a two stage process for preparing 2,4-dichlorobenzyl alcohol from 2,4-dichlorobenzl chloride in which the first stage comprises reacting the 2,4-dichlorobenzyl chloride with a water soluble salt of an organic acid in the presence of a phase transfer catalyst to give the 2,4-dichlorobenzyl ester of the organic acid and the second stage comprises the hydrolysis of the 2,4-dichlorobenzyl ester of the organic acid with a strong base to give 2,4-dichlorobenzyl alcohol.

The process of the present invention has a number of advantages over the preparation of the alcohol in which the chloride is directly hydrolysed by a strong base. In this reaction alcohol is formed in the presence of chloride resulting in by-product formation of bis-2,4 dichlorobenzyl ether. This results in a reduction of yield of the desired product and necessitates the use of a further purification stage to remove the unwanted by-product. The two-stage process of the present invention prevents the production of any appreciable amounts of this unwanted by-product and facilitates the achievement of a high yield of the desired product.

Several other methods of manufacture of benzyl alcohols including 2,4-dichlorobenzyl alcohol are described in British Patent Specification No. 1431238 published in 1976 in the name of Bayer Aktiengesellschaft. These methods include (a) the catalytic hydrogenation of the corresponding benzaldehyde (for example with hydrogen in tetrahydrofuran over a Raney nickel catalyst), (b) the reduction of the corresponding carboxylic acid with, for example, lithium aluminium hydride and (c) the reduction of the corresponding carboxylic acid halides with, for example, sodium borohydride. These proposed reactions all involve the use of expensive reduction techniques.

The use of phase transfer catalysts in the preparation of benzyl esters from benzyl halides having no ring substituents is described in the literature. See, for example, (a) "Compendium of phase-transfer reactions and related synthetic methods" edited by W. E. Keller published by Fluka AG in 1979 at page 28,
(b) An article by H. Normant, T. Cuvigny and P. Savignac entitled "Catalytic Activation of Anions by Polyamines in Two Phase Solid/Liquid Media" in Synthesis 1975 p805, and
(c) "Phase Transfer Catalysis" by E. V. and S. S. Dehmlow published by Verlag Chemie as No. 11 in a series of Monographs in Modern Chemistry at page 73.

The above references do not, however, describe the reaction of benzyl chlorides which have ring substituents and do not, in particular describe the use of phase transfer catalysts in the reaction of 2,4-dichlorobenzyl chloride. Examples of phase transfer catalysts which may be used in the first stage of the process of the invention include alkylammonium salts e.g. tetrabutylammonium salt such as the hydrogen sulphate or a halide e.g. the iodide, long chain alkylammonium halides e.g. tetradecyltrimethylammonium bromide; arylkylammoniumm compounds, e.g. benzyltriethylammonium chloride or hydroxide and alkylphosphonium halides, e.g. hexadecyltributylphosphonium bromide.

Preferably the water soluble salt is an alkali metal salt, usually a sodium or potassium, preferably sodium, salt of a preferably weak organic acid, e.g. a $C_2$ or higher fatty acid and especially acetic acid. Other salts may include e.g. ammonium salts.

The resulting ester is generally hydrolysed with an aqueous alkali e.g. sodium hydroxide.

Both reactions are preferably carried out in an aqueous medium at a temperature of e.g. 70° to 150° C., preferably 70° to 80° C.

The invention is illustrated in the following Examples.

EXAMPLE 1

2,4-Dichlorobenzyl chloride (100 g) was added to a solution of sodium acetate (208.8 g) and tetrabutylammonium hydrogen sulphate (2 g) in water. The mixture was heated under reflux with stirring for 25 hours. Aqueous sodium hydroxide (50 ml. of 70% w/v solution) was added and the refluxing continued for 30 minutes. The mixture was cooled and the solid collected by filtration, washed with water and dried in vacuo to give 2,4-dichlorobenzyl alcohol, having a purity of 99.3%, in a yield of 94.6%.

EXAMPLE 2

Aqueous sodium hydroxide (36 ml. of 70% w/v solution) was added slowly with stirring to glacial acetic acid (39 g). The solution was then heated to reflux and a mixture of 2,4-dichlorobenzyl chloride (100 g) and tetrabutylammonium iodide (1 g) added. The mixture was heated under reflux with stirring for 7 hours. The mixture was then treated with aqueous sodium hydroxide and worked up as described in Example 1 to give 2,4-dichlorobenzyl alcohol, having a purity of 98.5% in a yield of 95.0%.

EXAMPLE 3

Aqueous sodium hydroxide (40 ml of 70% w/v solution) was added slowly with stirring to glacial acetic acid (42 g). The temperature rose to reflux and tetrabutylammonium hydrogen sulphate (0.5 g) and 2,4-dichlorobenzyl chloride (100 g) were added and the mixture heated under reflux for eight hours. The mixture was cooled to 70°–75° C. and aqueous sodium hydroxide (35 ml of 70% w/v solution) added. The temperature was maintained in the range 70°–75° C. for 30 minutes. The product was extracted into petroleum ether (boiling range 80°–100° C. 90 ml) at 75° C. and the organic extract was diluted with petroleum ether (150 ml), washed with dilute aqueous hydrochloric acid, and filtered. The filter was washed with petroleum ether (40 ml) and the filtrate and washings combined and allowed to cool to give crystals of 2,4-dichlorobenzyl alcohol having a purity of 99.8% and in a yield of 95%.

I claim:
1. A two stage process for preparing 2,4-dichlorobenzyl alcohol from 2,4-dichlorobenzyl chloride in which

(a) the first stage comprises heating 2,4-dichlorobenzyl chloride and an aqueous solution of a water soluble salt of an organic acid selected from the group consisting of sodium acetate, potassium acetate and ammonium acetate under reflux in the presence of a phase transfer catalyst selected from the group consisting of alkylammonium salts, long chain alkylammonium halides, arylalkylammonium compounds and alkylphosphonium halides and in the absence of any organic solvent to form the 2,4-dichlorobenzyl ester of the organic acid; and (b) the second stage comprises heating the 2,4-dichlorobenzyl ester with a strong base to hydrolyse the ester to give 2,4-dichlorobenzyl alcohol.

2. The process according to claim 1 in which the alkali metal salt is sodium acetate.

3. The process according to claim 1 in which the strong base is sodium hydroxide.

4. The process according to claim 1 in which the phase transfer catalyst is a tetrabutylammonium salt.

* * * * *